(12) United States Patent
Zaitsev

(10) Patent No.: US 7,794,598 B2
(45) Date of Patent: Sep. 14, 2010

(54) BIOREACTOR AND METHOD FOR THE BIOLOGICAL PURIFICATION OF WATER

(75) Inventor: Gennadi Zaitsev, Rovaniemi (FI)

(73) Assignee: Clewer Oy, Riihimaki (FI)

( * ) Notice: Subject to any disclaimer, the term of this patent is extended or adjusted under 35 U.S.C. 154(b) by 184 days.

(21) Appl. No.: 12/085,584

(22) PCT Filed: Dec. 22, 2006

(86) PCT No.: PCT/FI2006/050587

§ 371 (c)(1), (2), (4) Date: Jun. 18, 2008

(87) PCT Pub. No.: WO2007/077298

PCT Pub. Date: Jul. 12, 2007

(65) Prior Publication Data

US 2009/0272688 A1    Nov. 5, 2009

(30) Foreign Application Priority Data

Jan. 4, 2006    (FI) .................................. 20065006
Jan. 10, 2006    (FI) .................................. 20065013

(51) Int. Cl.
  *C02F 3/06* (2006.01)
  *C02F 3/30* (2006.01)
(52) U.S. Cl. .................. 210/605; 210/616; 210/617; 210/629; 210/150
(58) Field of Classification Search .................. 210/605, 210/616, 617, 629, 630, 150, 151
  See application file for complete search history.

(56) References Cited

U.S. PATENT DOCUMENTS 2,071,591 A * 2/1937 Tholin .................. 210/616
4,009,099 A * 2/1977 Jeris .................. 210/151

(Continued)

FOREIGN PATENT DOCUMENTS

GB    2 132 503    7/1984

(Continued)

*Primary Examiner*—Christopher Upton
(74) *Attorney, Agent, or Firm*—Dennison, Schultz & MacDonald

(57) ABSTRACT

The invention relates to a bioreactor (1) for the purification of waters, said reactor comprising a cross-sectionally essentially circular or elliptical tank section (2) provided with inlet means (5) for water to be purified and outlet means (6) for purified water. The tank holds thereinside carrier material (3) on which a biofilm may develop. The tank is further provided with means (4) for supplying a fluid which contains a reaction gas required by the purification process, such that the water to be purified develops gas bubbles containing a reaction gas. The tank section is adapted to be essentially full of water during the purification process. The fluid supply means (4) are disposed on the tank wall and the reactor comprises control means for operating the fluid supply means in such a way that a spinning motion of the carrier, the water, and at least some of said reaction-gas bearing bubbles is effected thereby around a rotation centerline passing essentially through the tank's cross-sectional center. The control means are adapted to optionally effect a deactivation of the fluid supply means at desired times and/or a replacement of the fluid with an oxygen-free fluid for providing an anaerobic process. The invention relates also to a method for the biological purification of waters in a bioreactor.

15 Claims, 2 Drawing Sheets

U.S. PATENT DOCUMENTS

| | | | |
|---|---|---|---|
| 4,200,532 A * | 4/1980 | Iwatani et al. | 210/151 |
| 4,325,823 A * | 4/1982 | Graham | 210/532.2 |
| 4,655,925 A * | 4/1987 | Tabata et al. | 210/605 |
| 4,663,046 A | 5/1987 | Feldkirchner et al. | |
| 4,705,634 A * | 11/1987 | Reimann et al. | 210/616 |
| 4,917,805 A * | 4/1990 | Reid | 210/605 |
| 5,198,105 A | 3/1993 | Kauling et al. | |
| 5,413,749 A | 5/1995 | Geiser | |
| 5,674,802 A | 10/1997 | Sheppard | |
| 6,447,675 B1 * | 9/2002 | James | 210/150 |
| 6,955,757 B1 * | 10/2005 | Maltin | 210/150 |

FOREIGN PATENT DOCUMENTS

| | | |
|---|---|---|
| JP | 4094800 | 3/1992 |
| JP | 9052096 | 2/1997 |
| WO | WO 96/10542 | 4/1996 |

* cited by examiner

BIOREACTOR AND METHOD FOR THE BIOLOGICAL PURIFICATION OF WATER

This application is a 371 of PCT/FI2006/050587 filed on Dec. 22, 2006.

The invention relates to a bioreactor for the purification of waters, said reactor comprising a cross-sectionally essentially circular or elliptical tank section provided with inlet means for water to be purified and outlet means for the purified water, said tank holding thereinside carrier material on which a biofilm may develop, and said tank being further provided with means for supplying air required by an aerobic purification process.

The invention relates also to a method for the biological purification of water in a bioreactor, which comprises a cross-sectionally essentially circular or elliptical tank section provided with inlet means for water to be purified and outlet means for the purified water, said tank holding thereinside carrier material on which a biofilm may develop, and said tank being further provided with means for supplying air required by an aerobic purification process.

The biological purification of water, such as e.g. waste water, the water is passed through a reactor, wherein micro-organisms are utilized for converting water-borne impurities into harmless end products such as carbon dioxide, minerals and water. In biological water purification, the micro-organisms may have bonded to themselves, i.e. to the biomass, also non-biodegradable products, e.g. heavy metals. Purification can be performed aerobically or anaerobically. Prior known are various bioreactors for waste water purification, such as trickling filters, biorotors (rotating biological contactors), fluidized bed reactors, fixed bed reactors, and moving bed reactors. One prior known bioreactor comprises conveying a carrier material to a process, the surface of said carrier material being able to grow micro-organisms in the form of a biofilm.

One typical biofilm process (fixed bed reactor) is based on filling the purification reactor with a carrier material in the form of filler particles, said filler particles being adapted to remain stationary during the process. The oxygenation of a biofilm present on the surface of filler particles is effected by supplying the reactor with air through the bottom. An advantage of the process is a large amount of biomass per unit volume of the reactor as the biofilm has a large growth area. A drawback in this type of so-called fixed bed is that the bioprocess can be brought to a standstill by biomass (sludge) or other particulate matter, and that inactive zones may develop in the process in places with a poor contact between water and active micro-organisms. Another problem is difficult cleaning because of a difficult access below a reactor and, should a bioreactor become clogged, the entire bioreactor volume must be vacated for cleaning.

Prior known are also biofilm processes, wherein the carrier material is kept in motion during the process, see e.g. U.S. Pat. Nos. 6,126,829, 5,458,779, and 5,543,039. An advantage in such a moving bed type bioreactor is that the clogging of a carrier material and the development of inactive zones are substantially eliminated. The surface of carrier elements is partially protected against collisions with other carrier elements. A drawback here is, however, a considerably limited capacity of the process due to the fact that a particularly low degree of filling is required, e.g. in the order of about 30-70% of an empty reactor volume, in order to provide the carrier elements with unrestricted mobility in water to be purified. Accordingly, the capacity of eliminating impurities is lower than that of a fixed bed reactor which has the same volume and is filled with the same carrier material, because the fixed bed reactor has a higher loading capacity.

Increasing the degree of filling would result in increased oxygen consumption, which would require a more powerful compressor, whereby the powerful blasting may further disturb the bioprocess. Increasing the degree of filling would lead to the formation of a fixed bed and would bring the biological process to a standstill as the carriers would become clogged by biomass. In addition to this, if the degree of filling in a moving bed type of reactor were to be increased, it would require an adversely large amount of air and energy for keeping the carriers moving, which in turn would remarkably increase the mechanical stress applied to a biofilm and this, in turn, would lead to the biofilm peeling off the carrier surface, which would in turn result in a standstill of the biological process. Another major drawback is that the reactor must be provided with a safety screen for separating the aeration means from carrier elements. The screen must have such a mesh size as to deny the passage of carrier elements through the openings. This precludes the use of small-size carriers which would provide a large area per unit volume, because a corresponding downsizing of the screen's mesh size would undermine air supply and would be likely to cause blocking of the openings.

An object of the present invention is to provide an improved bioreactor capable of eliminating the drawbacks of both a fixed bed process and a moving bed process, accomplishing a higher rate treatment of impurities per unit volume than what is achieved by prior known reactors, and thereby to reduce purification costs. In order to accomplish this objective, a bioreactor of the invention is characterized in that the tank section is essentially circular or elliptical in cross-section, that the water outlet means are provided in the tank section in such a way that the tank section is essentially full of water during the purification process, that the fluid supply means are disposed on the tank wall, and that the reactor comprises control means for operating the fluid supply means in such a way that a spinning motion of the carrier, the water, and the reaction-gas bearing fluid is effected thereby around a rotation centerline passing essentially through the tank's cross-sectional center, the control means being adapted to optionally effect a deactivation of the fluid supply means at desired times.

An idea of the invention, according to which the tank section is maintained essentially filled with water during the purification process, enables a reaction gas, e.g. in the form of gas bubbles, to travel along with water and a carrier, thus giving the bubbles a long effective distance and time, thus allowing a high degree of filling for the carrier, preferably within the range of more than 70% to about 100%, as opposed to the prior known moving bed type of solution which teaches that the degree of filling of a carrier material lies within the range of 30-70%. The degree of filling of a carrier material is in direct proportion to the performance of a biological process, i.e. the higher the degree of filling of a carrier material in a reactor $m^2/m^3$, the higher its purification performance. In a solution according to the present invention, the quantity of a carrier material may also be distinctly less than 70%, e.g. less than 50%. The degree of filling for a carrier material is determined on the basis of the oxygenation capacity and loading of a reactor. Carriers may consist of pieces of plastic with a desired size and shape to enable sustained spinning motion. When using a reactor of the invention, it has been found in an aerobic process that air bubbles remain in the reactor for a considerably longer time than in currently used reactors, since the air bubbles are spinning for quite some time along with the carrier material and water for a more effective oxygenation of biofilm. Simultaneously, the air bubbles break up into smaller ones, which is another factor contributing to the transfer of oxygen from air into water. This reduces the demand of air and consequently reduces operating costs compared with activated sludge, fixed bed, and moving bed type of processes.

On the other hand, a method of the invention is characterized in that, in a bioreactor used in the method, the tank section is essentially circular or elliptical in cross-section and the fluid supply means are disposed on the tank wall, that the method comprises supplying the tank with unpurified water such that the tank is essentially full of water during the purification process, and that the fluid supply means are controlled in such a way that a spinning motion of the carrier, the water, and the reaction-gas bearing fluid is effected thereby continuously or intermittently around a rotation centerline passing essentially through the tank's cross-sectional center.

A solution of the invention enables a large growth area for biofilm and the reactor does not develop dead zones with the carrier, the water, and the reaction-gas bearing fluid spinning at a roughly consistent angular velocity around a rotation centerline in a single section. Various sections in a bioreactor may nevertheless move in different directions.

A rotary type of bioreactor of the invention, in which carrier elements are spinning in one and the same direction, distinguishes itself clearly from a moving bed type process of the prior art, in which carrier elements are moving in chaotic order in water, only allowing the use of a relatively low degree of filling. Should the degree of filling be in excess of 70%, the moving bed type of process would turn into a fixed bed type as the particles in chaotic motion would collide with each other at higher frequency and this would bring the motion thereof to a standstill and result in the clogging of a bioreactor. It is a particularly advantageous feature that, according to the invention, the tank section is adapted to be full of water during operation, whereby the energy needed for spinning a carrier material is at its minimum and at the same the gas bubbles spin, the same way as the carrier material, along with water around a rotation centerline, whereby the effective distance and time thereof become multiple, when compared e.g. with a prior known type of moving bed solution, which involves the use of a liquid level and in which the air bubbles only migrate essentially from the inlet point of air, which is typically at the bottom of a tank, to an air space present in the top portion of the tank. In this disclosure, the term "essentially full of water" is used in reference to the tank containing so much water that the supply of a fluid is able to set the carrier, the water, and the reaction-gas bearing fluid in a spinning motion around a rotation centerline passing essentially through the tank's cross-sectional center. It has been found experimentally that the amount of water should be more than at least about 85%, preferably about 100%, of the cross-sectional diameter. In the event that the amount of water is less than about 85%, the process becomes a moving bed type of process, in which the degree of filling of a carrier material must be less than 70% for the process to work rather than to turn into a fixed bed type. Another reason why the moving bed type of solution uses a relatively low degree of filling and carrier elements are shaped in a specific manner is to protect the biofilm from damage caused by carrier elements colliding repeatedly with each other. The solution according to the present invention uses preferably a semifixed bed solution, in which the carrier material consists of a plurality of carrier elements having a degree of filling in the tank section of about 100% and, consequently, not essentially moving relative to each other while spinning around a center centerline but, instead, are spinning in the form of a essentially integral carrier bed. Thus, the composition of carrier elements is not as critical as in a moving bed type solution, in which the movement of carrier elements relative to each other must be taken into consideration. A solution of the invention allows for using a more delicate fluid blast, which does not upset bacteria on the surface of a carrier material since, by virtue of an optimal rotating motion, the method of the invention does not require a large amount of fluid for sustained movement of the carrier. What is essential from the viewpoint of biology is that the biofilm not become mechanically flushed off the carrier surface by gas bubbles. Since the supply of fluid is located on the outer periphery and carriers do not move relative to each other, no mechanical stress will be inflicted by this either, largely because of a high degree of filling of over 70%. On the other hand, the excess sludge or dead biomass is forced out the bioreactor by the law of inertia. If, in a rotating motion, a biomass starts to accumulate towards the origo, it is there that the density also begins to increase, the consequence of which is, in turn, that carriers present in the middle begin a gradual migration towards the outer periphery and the biomass is on the outer periphery able to emerge out of the bioreactor in response to the law of inertia.

The degree of filling of a carrier material is a term used in reference to the amount of space required by a carrier material with respect to a tank section's volume in its empty condition, not in reference to the volume of water displaced thereby. When using a plurality of carrier elements, the 100% degree of filling is indicative of the fact that no more carrier elements can be fitted in the volume of a tank section.

The invention will now be described in more detail with reference to the accompanying drawings, in which.

Figure 1:
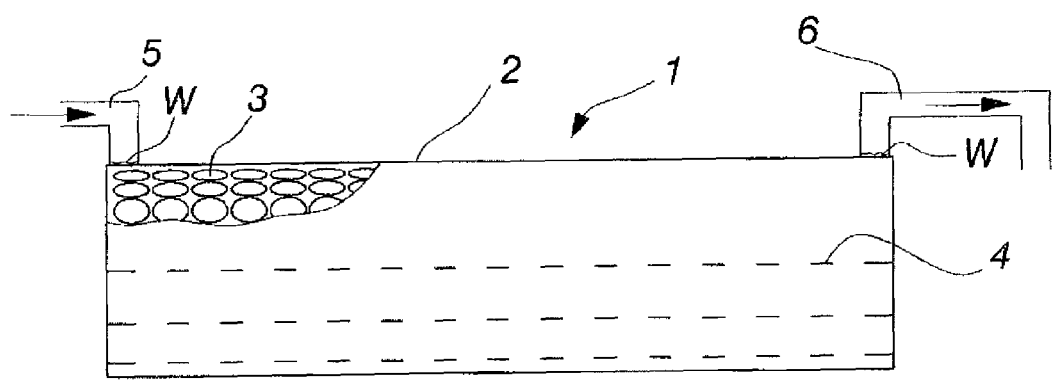
FIG. 1 shows one bioreactor according to the invention in a schematic side view.
Figure 2:
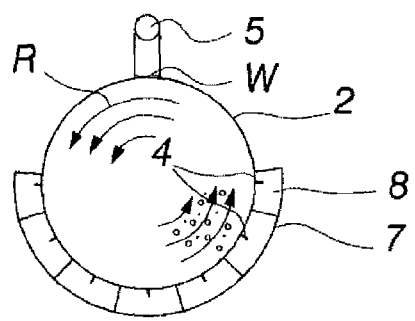
FIG. 2 shows the reactor of FIG. 1 in an end view.

As shown in the figures, a bioreactor 1 of the invention comprises a tubular tank section 2, which is preferably circular or elliptical in cross-section. The tank section 2 is provided with inlet means 5 for water to be purified and outlet means 6 for the purified water, as well as with means 4 for supplying a fluid containing a reaction gas required by the purification process, preferably in such a way that the water to be purified develops reaction-gas bearing gas bubbles, such as for supplying air, in the form of air bubbles, required e.g. by an aerobic purification process, from which the air dissolves in water for oxidizing the same for bacterial activity. The fluid may also consist of pre-aerated water with air present in the form of air bubbles and/or in a previously dissolved form to provide oxygen-rich water. In the illustrated case, depicted only by way of example, the inlet means 5 and outlet means 6 for water are disposed at the longitudinally opposite ends of a tank section 2 in the top portion of the tank section. The inlet and/or outlet means can be located also elsewhere in the tank section 2, in an arrangement such that the supply of unpurified water and the discharge of purified water can be performed in such a way that the tank section 2 is essentially full of water during the purification process. In the figures, the level of water is designated with reference character W. The supply of water to be purified proceeds preferably in continuous action, e.g. by having a balancing reservoir upstream of the bioreactor for collecting water to be purified and pumping it therefrom in a continuous feed by way of a tube 5 to the bioreactor. The supply of water to be purified can proceed also in a batch type process, whereby the tank section is supplied with water to be purified to its capacity, an air blast is commenced for spinning motion and oxygenation and, once the purification process is over, the air blast is discontinued and the tank section is vacated of purified water, followed by restarting the process.

Inside the tank section is provided a carrier material 3, on which micro-organisms may deposit as a biofilm. The carrier material may consist e.g. of a single carrier element or a plurality of firmly joined carrier elements or a plurality of discrete carrier elements, whereby, in the latter case, the carrier elements can be identical or dissimilar to each other, e.g. in terms of the size, shape, density and/or other properties thereof.

In the exemplary case of FIG. 1, a tank has been loaded with a plurality of discrete carrier elements 3 almost to the 100% degree of filling, such that said-particles are capable of making a spin around the tank's longitudinal centerline by virtue of the tank element's circular or elliptical cross-section as a essentially integral carrier bed in a determined sense of rotation. The internal surface of a tank section 2 is essentially smooth for unhindered spinning of the carrier, the air supply means being disposed at the tank element's 2 external surface. In the illustrated embodiment, the air supply means 4 are disposed in supply passages 8, which are arranged within a protective cover 7 surrounding the tank at least partially and which are each connected by way of a valve element (not shown) to a source of inlet air. Each passage 8 includes preferably several air supply means or nozzles 4 in succession lengthwise of the tank, but can also be provided with a single integral nozzle member covering the tank essentially over its entire length. Each nozzle member 4 can be provided with an aeration element, e.g. a membrane, which during a normal supply air flow allows for the flow of supply air into the tank while precluding the admission of water to be purified present in the tank into the passage 8. The membrane is useful in attaining a smaller size of the air bubble, and the smaller the size of an air bubble the lesser its buoyancy, and thereby the smaller air bubble spins around more effortlessly in a bioreactor codirectionally with carriers. The aeration element may also be comprised e.g. of an apertured tube or air holes in the walls of a bioreactor. In front of the air nozzles can be disposed a safety screen, preventing the air bubbles from hitting the carrier material in a biofilm damaging manner. In connection with the outlet tube 6 is preferably disposed a vent pipe (not shown) for removing excess air from the tank. The tank section's 2 top side can be provided with tiny vent holes (not shown), the function of which is to avoid the development of possible air pockets in the upper portion of a tank, which could slow down the spinning of water in the tank, thus increasing energy consumption. Such vent holes are preferably connected to a vent pipe (not shown) disposed e.g. in connection with the outlet tube 6. The tank 2 is preferably set in a horizontal position and the passages 8 are positioned in and/or below a longitudinal median plane of the tank 2. In the case of a tank which is e.g. essentially circular in cross-section, the nozzle members 4 can be placed e.g. at one or more positions coincident with 3, 4, 5, 6, 7, 8 and 9 o'clock positions in a normal clock face. In association with the reactor is further provided a logic control, whereby the supply valve of various passages can be optionally switched off and thus, by closing for example the passages 8 with nozzle members located at positions from 6 to 9 o'clock, the air flow proceeding through nozzle members present at positions from 3 to 5 o'clock brings about a spin of the carrier material in the tank around the tank's longitudinal centerline. Such an intermittent spinning drive of carrier material can be e.g. about 1 minute per every other hour. Naturally, the cyclicity can be even drastically other than that, both in terms of spinning time duration and repetition frequency. In addition, the cyclicity can be irregular. Another way of implementing a bioreactor of the invention by adapting the air supply to spin-drive carrier elements during the purification process in continuous action around a longitudinal centerline for a dynamic consistent motion effective in removing sludge from the reactor. In this case, the tank 2 is only provided with one aeration element, preferably e.g. at a 3 or 9 o'clock position, which aeration element can be e.g. a single air supply passage 8 provided with its nozzle members and extending lengthwise of the tank 2, which nozzle members can be e.g. in the form of aeration holes made in the tank's 2 wall in coincidence with the passage. When the employed fluid comprises a reaction-gas containing liquid, in which the reaction gas is in an already-dissolved state and does not essentially contain gas bubbles from which the reaction gas must first dissolve in water, e.g. dissolved-air containing water, the supply of fluid can be implemented basically from anywhere along the tank's periphery, e.g. from a position in the vicinity of 12 o'clock.

One of the benefits offered by a solution of the invention is e.g. avoiding the turbulence-inflicted deceleration of a microbiological process, which is what happens in a process with carrier elements moving constantly in random directions. In addition, the degree of filling can be made essentially higher than in a moving bed type of process. When compared to a fixed bed process, in which the carrier remains essentially stationary throughout the process, a solution of the invention is capable of using smaller-size carriers whose surface area per cubic unit of a bioreactor is larger, resulting in an increased cleaning capacity. In a fixed bed process, the size of carrier elements must be relatively large for the sludge-inflicted clogging thereof. By virtue of the regular spinning motion of a carrier material according to the invention, effected in intermittent or continuous action, there is no accumulation of sludge comparable to a fixed bed process.

Another mode of operation for a bioreactor of the invention is such that the air supply is periodically discontinued completely for converting the process from aerobic to anaerobic for allowing the use of one and the same bioreactor volume for denitrification in which nitrogen, present as a nitrate, is reduced to nitrogen gas ($NO_3^- \rightarrow NO_2^- \rightarrow NO \rightarrow N_2O \rightarrow N_2$).

A bioreactor of the invention can be used e.g. as part of a purification system for the black and/or grey waste waters of a single house, such that the bioreactor is preceded by a septic section and an anaerobic section, followed by bringing water to be purified into the bioreactor for aerobic treatment. The bioreactor is preferably followed by yet a second aerobic bioreactor capable of performing nitrification ($NH_3 \rightarrow NO_2^- \rightarrow NO_3^-$), after which the water is delivered to a denitrification process. Finally, the purified water is delivered to a phosphor precipitation section and to a secondary settling tank. Naturally, a bioreactor of the invention is indeed useful in a wide range of applications, such as sewage works, car washes, laundries, fish farms, and in the purification of e.g. swimming pool cleaning waters, landfill seep waters, mine waters, industrial suds and washings, and waste waters from flue gas scrubbers or the like, and there may be a number of bioreactors in succession and/or side by side.

A bioreactor of the invention can also be implemented in such an embodiment that the tank section is divided for two or more sections, whereby some of the sections may work aerobically, i.e. have an air supply adapted to set a carrier, air bubbles and water in spinning motion during the purification process in continuous action, and the other sections may work anaerobically. In an anaerobic process, the supply of a fluid enabling rotation is intermittent or optionally the carrier material is set in a continuous or cyclic spinning motion by recirculating water or other fluid, which does not contain dissolved oxygen and/or oxygen-bearing gas bubbles in the amount required by an aerobic process, by way of openings present in the reactor wall.

The spinning motion can also be produced by a fluid other than air, e.g. by water, which is pre-aerated prior to its delivery into a tank section containing water to be purified and which water is delivered in such a manner that the air borne therein produces bubbles in the tank section containing water to be purified. The pre-aerated water may contain its air also in a essentially dissolved state, in which case the dissolved-air bearing, oxygen-rich water may function in an aerobic process even without a substantial formation of bubbles. The purification process can also be a process calling for a gas other than oxygen, in which case the fluid to be supplied can be a gas or gas mixture other than air or it can also be water or other liquid containing the reaction gas.

A solution of the invention can be implemented not only by means of a tubular elongated tank section but also a tank section which is essentially spherical, wherein the carrier material is spinning symmetrically in one direction around a rotation centerline passing through the sphere's center. As described above, the carrier material may consist e.g. of a single carrier element or a plurality of firmly joined carrier elements or a plurality of discrete carrier elements, whereby, when using a plurality of carrier elements, the latter can be identical or dissimilar to each other e.g. in terms of the size, shape, density and/or other properties thereof. Thus, in the sense of vertical cross-section, the air supply means are positioned between 3 to 9 o'clock, such that the spinning motion created thereby proceeds preferably around a essentially horizontal rotation centerline. The tank section is conceivable also as an structure having a form of an ellipsoid or ellipsoid generated by rotation or e.g. as a puck or disc like short tube with a essentially circular cross-section and a length which is in the same range as or shorter than the cross-sectional diameter.

The carrier material useful in a bioreactor of the invention may consist of an ion exchanger or contain an ion exchanger, e.g. a ceramic material. The use of an ion exchanger enhances denitrogenation, the nitrogen being captured by the ion exchanger and eaten by bacteria. Preferably, the carrier material comprises a polymer-ceramic composite, e.g. a polymer-zeolite composite.

The amount of water in a tank being about 100%, e.g. by disposing the water inlet and outlet tubes such that the surface of water lies above the tank, the carrier elements heavier than water are precluded from leaving the body of water without other measures, even if the carrier elements had been given an extraordinarily small size.

The carrier element is preferably spherical in shape for achieving optimal spinning of the carrier material in a tank section, and an optimal degree of filling is also obtained. The spherical carrier element can be e.g. as described in GB patent 2197308, wherein the water to be purified can flow through a carrier element, or e.g. a solid ball element, having its surface provided with hemispherical depressions in which a biofilm can develop safely from being contacted by adjacent carrier elements.

Figure 3:
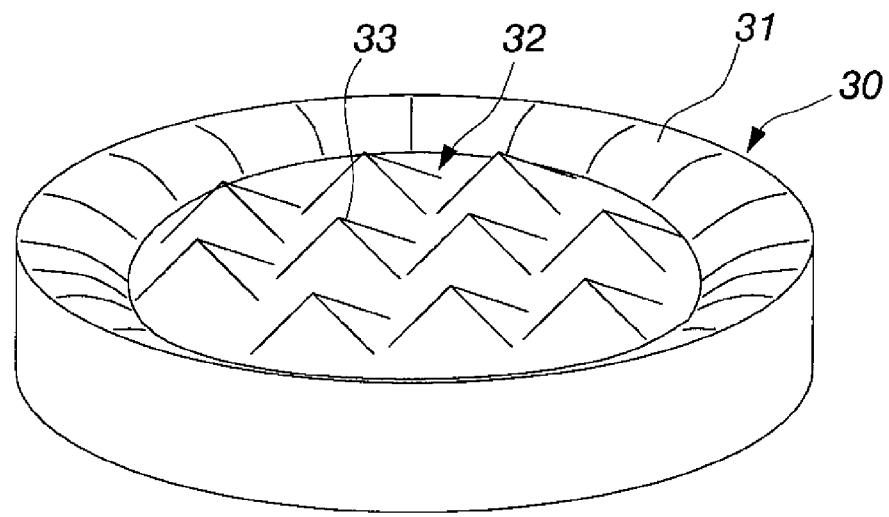
FIG. 3 shows one carrier element of the invention in a schematic view of principle.
Figure 4:
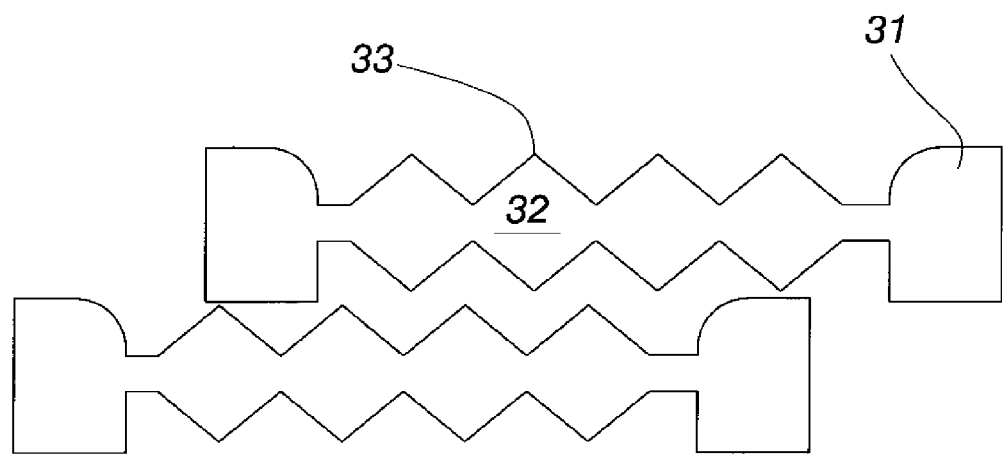
FIG. 4 shows two carrier elements of FIG. 3 in cross-sectional views set in an exemplary relation to each other.

One alternative shape for a carrier element is a disck-like element 30 shown in FIGS. 3 and 4 which comprises a middle section 32, which is reduced in thickness relative to a rim section 31 and which is formed with pyramidal protrusions 33 which accomplish a multiplication of a biofilm growth area as compared with a smooth particle and at the same time protect the biofilm as collisions occuring with adjacent carrier elements. The middle section can also be provided with through-holes. The disc 30 may have a diameter e.g. in the order of about 5 mm, and its thickness at the rim section 31 can be e.g. about 1 mm while its density is about 1.1 kg/m$^3$. These values are of course given only as suggestive non-limiting examples and the shape, size and density of carrier elements may deviate considerably from the foregoing. This type of carrier element is also conceivable for use e.g. in a moving bed type of bioreactor.

The invention claimed is:

1. A bioreactor for the purification of water, said bioreactor comprising:
   a tank provided with inlet means for carrying the water to be purified, and means for supplying a fluid which contains a reaction gas required by the purification process;
   outlet means for carrying the purified water;
   a carrier material on which a biofilm can develop; said carrier material being disposed inside the tank; said carrier material comprising one or more carrier elements having a degree of filling in the tank of more than 70% to about 100%;
   wherein the tank is essentially circular or elliptical in cross-section;
   wherein the water outlet means is provided in the tank in such a way that the tank is essentially full of water during the purification process;
   wherein the fluid supply means is disposed on the tank wall; and
   wherein the reactor comprises a control means for operating the fluid supply means in such a way that a spinning motion of the carrier, the water, and the reaction-gas bearing fluid is effected thereby around a rotation centerline passing essentially through a cross-sectional center of the tank.

2. A bioreactor as set forth in claim 1, wherein the tank has an internal surface made essentially smooth, allowing for unhindered spinning of the carrier material around a longitudinal centerline.

3. A bioreactor as set forth in claim 1, wherein the purification process is adapted to proceed as an aerobic process, and wherein said reaction-gas containing fluid comprises air which is supplied into the tank containing water to be purified in a way to produce bubbles from which the air dissolves in the water.

4. A bioreactor as set forth in claim 3, wherein around the tank is provided a protective cover, enclosing the tank at least partially and featuring at least one air supply passage which is connected by way of a valve means to a source of supply air and which passage is fitted with the fluid supply means disposed on the tank wall.

5. A bioreactor as set forth in claim 4, wherein the air supply means present in the passage comprises a plurality of nozzle members arranged in succession in a longitudinal direction of the passage.

6. A bioreactor as set forth in claim 5, wherein each nozzle member is provided with a membrane, which allows for a flow of supply air into the tank while essentially blocking the admission of unpurified water in the tank into the passage.

7. A bioreactor as set forth in claim 4, wherein the air supply means comprises aeration vents made in the wall of the tank in alignment with said at least one passage.

8. A bioreactor as set forth in claim 1, wherein the purification process is adapted to proceed as an anaerobic process, such that the control means is adapted to optionally effect a deactivation of the fluid supply means at desired times and/or a replacement of the fluid with one essentially free of a reaction gas.

9. A bioreactor as set forth in claim 1, wherein control of the fluid supply means is implemented as a logic control.

10. A bioreactor as set forth in claim 1, wherein the tank is an elongated tubular or discoid structure disposed in an essentially horizontal position.

11. A bioreactor for the purification of water, said bioreactor comprising:
   a tank provided with inlet means for carrying the water to be purified, and means for supplying a fluid which contains a reaction gas required by the purification process;
   outlet means for carrying the purified water;
   a carrier material on which a biofilm may develop; said carrier material being disposed inside the tank; said carrier material comprising a plurality of carrier elements having a degree of filling in the tank of about 100%, thus spinning in the form of an essentially continuous carrier bed around the rotation centerline upon supplying the tank with said fluid;
   wherein the tank is essentially circular or elliptical in cross-section;
   wherein the water outlet means is provided in the tank in such a way that the tank is essentially full of water during the purification process;
   wherein the fluid supply means is disposed on the tank wall; and
   wherein the reactor comprises a control means for operating the fluid supply means in such a way that a spinning motion of the carrier, the water, and the reaction-gas bearing fluid is effected thereby around a rotation centerline passing essentially through a cross-sectional center of the tank.

12. A method for the biological purification of water in a bioreactor, said method comprising:
   providing a tank with inlet means for carrying the water to be purified, and outlet means for carrying the purified water;
   said tank having a means for supplying a fluid which contains a reaction gas required by the purification process, said fluid supply means being provided on the tank wall; wherein the tank is essentially circular or elliptical in cross-section; comprises:
   providing a carrier material on which a biofilm can develop, said carrier material being disposed inside the tank;
   said carrier material comprising one or more carriers, wherein the carrier material has a degree of filling in the tank within the range of more than 70% to about 100%;
   supplying the tank with water to be purified such that the tank is essentially full of water during the purification process; and
   controlling the fluid supply means in such a way that a spinning motion of the carrier, the water, and the reaction-gas bearing fluid is effected thereby continuously or intermittently around a rotation centerline passing essentially through a cross-sectional center of the tank.

13. A method as set forth in claim 12, wherein the purification process is adapted to proceed as an aerobic process, and wherein air is used as said reaction-gas bearing fluid, wherein said air produces bubbles in the water to be purified, wherein at least some of the air bubbles spin, along with the carrier material and the water, around said rotation centerline.

14. A method as set forth in claim 12, wherein the bioprocess is adapted to proceed as an aerobic process and that pre-aerated water is used as said reaction-gas bearing fluid, in which the air has dissolved and/or is present in the form of bubbles.

15. A method as set forth in claim 12, wherein the bioprocess is adapted to proceed optionally as an anaerobic process by deactivating the fluid supply at desired times and/or by replacing the fluid with one essentially free of a reaction gas.

* * * * *